(12) United States Patent
Mahabob

(10) Patent No.: US 11,806,056 B1
(45) Date of Patent: Nov. 7, 2023

(54) MINI-PLATE FOR BONE FRACTURE FIXATION

(71) Applicant: KING FAISAL UNIVERSITY, Al-Ahsa (SA)

(72) Inventor: Nazargi Mahabob, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/128,208

(22) Filed: Mar. 29, 2023

(51) Int. Cl.
*A61B 17/80* (2006.01)

(52) U.S. Cl.
CPC .................. *A61B 17/8052* (2013.01)

(58) Field of Classification Search
CPC . A61B 17/80; A61B 17/8052; A61B 17/8057; A61B 17/8061; A61B 17/82; A61B 17/823; A61B 17/826
See application file for complete search history.

(56) References Cited

U.S. PATENT DOCUMENTS

| | | | |
|---|---|---|---|
| 8,211,145 B2 * | 7/2012 | Dalton | A61B 17/8023 606/280 |
| 2005/0216008 A1 * | 9/2005 | Zwirnmann | A61B 17/68 606/915 |
| 2009/0030467 A1 | 1/2009 | Sonohata et al. | |
| 2011/0184414 A1 | 7/2011 | Andermahr et al. | |
| 2015/0289910 A1 | 10/2015 | Mirighasemi et al. | |

* cited by examiner

*Primary Examiner* — Si Ming Ku
(74) *Attorney, Agent, or Firm* — Nath, Goldberg & Meyer; Richard C. Litman

(57) ABSTRACT

The mini-plate for bone fracture fixation is a plate for internal fixation on a bone fracture having three linearly configured rings defined therein. The second and third rings have aligned gaps defined therein dimensioned and configured to permit the shank of the fixation screw below the screw head to gradually slide forward into the second ring as the fracture heals, narrowing the gap between the two sections or fragments of the fractured bone, leading to a more tightly knit union of the fractured bone. The third ring may have another gap defined therein at the free end of the plate to reduce drag and allow the shift from the third ring to the second ring to occur smoothly. The mini-plate installs quickly, requiring only two fixation screws, and promotes a more secure, stable union and reducing gaps in the healed fracture.

5 Claims, 1 Drawing Sheet

MINI-PLATE FOR BONE FRACTURE FIXATION

BACKGROUND

1. Field

The disclosure of the present patent application relates to treating bone fractures, and particularly to a mini-plate for bone fracture fixation.

2. Description of the Related Art

Broken bones (or fractured bones) are a commonplace occurrence in modern like. The physician has a number of options for treating the fractured bone, depending upon the circumstances, e.g., plaster casts, external braces, etc. One option available to the physician is internal fixation, which is a surgical approach in which the site of the fracture is opened, the surgeon manipulates the two fragments to approximate and properly align the bone fragments, and the fragments are internally fixed by stainless steel and/or titanium plates connecting the fragments, or simply by screws. The plates may be removed after healing, or may be left in the body, depending on the course of healing. The benefits of internal fixation include a reduced risk of non-union or misalignment of the bone during healing, as well as reduced hospital stay time and follow-up visits.

A variety of plates are available to the surgeon for internal fixation of fractured bones, most being entirely satisfactory. However, there is always a need for new variations to meet different facture presentations and provide advantages for particular situations. One problem common to all conventional plates is that once the plates are fixed by the screws, it is difficult to make adjustments for variations in the healing process of the fractured bone, i.e., once fixed, it stays fixed in that configuration. Thus, a mini-plate for bone fracture fixation solving the aforementioned problems is desired.

SUMMARY

The mini-plate for bone fracture fixation is a plate for internal fixation on a bone fracture having three linearly configured rings defined therein. The second and third rings have aligned gaps defined therein dimensioned and configured to permit the shank of the fixation screw below the screw head to gradually slide forward into the second ring as the fracture heals, narrowing the gap between the two sections or fragments of the fractured bone, leading to a more tightly knit union of the fractured bone. The third ring may have another gap defined therein at the free end of the plate to reduce drag and allow the shift from the third ring to the second ring to occur smoothly. The mini-plate installs quickly, requiring only two fixation screws, and promotes a more secure, stable union and reducing gaps in the healed fracture.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The mini-plate for bone fracture fixation is a plate for internal fixation on a bone fracture having three linearly configured rings defined therein. The second and third rings have aligned gaps defined therein dimensioned and configured to permit the shank of the fixation screw below the screw head to gradually slide forward into the second ring as the fracture heals, narrowing the gap between the two sections or fragments of the fractured bone, leading to a more tightly knit union of the fractured bone. The third ring may have another gap defined therein at the free end of the plate to reduce drag and allow the shift from the third ring to the second ring to occur smoothly. The mini-plate installs quickly, requiring only two fixation screws, and promotes a more secure, stable union and reducing gaps in the healed fracture.

Figure 1:
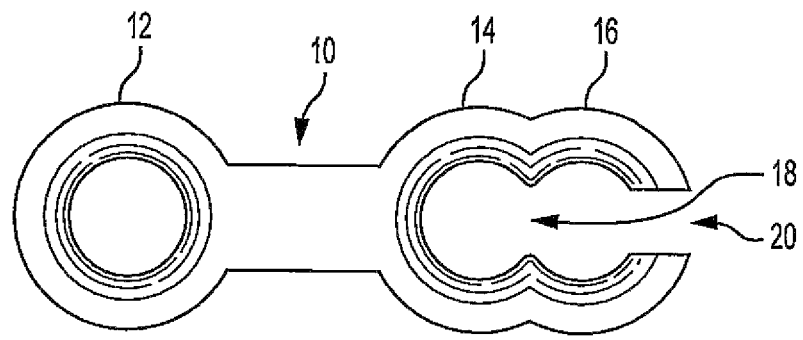
FIG. 1 is a perspective view of a mini-plate for bone fracture fixation.

As shown in FIG. 1, the mini-plate 10 is a small plate for internal fixation of a bone fracture made of stainless steel, titanium, or other biocompatible alloy and having a length of about four to five centimeters, for example. It will be understood that the drawing figures are not drawn to scale, but are more pictorial or schematic in nature in order to show the overall configuration and operation of the mini-plate. The mini-plate 10 has a first ring 12, a second ring 14, and a third ring 16 defined therein. The second ring 14 and the third ring 16 have aligned gaps 18 defined therein. In addition, the third ring as an additional gap 20 defined therein at the free end of the mini-plate.

Figure 2:
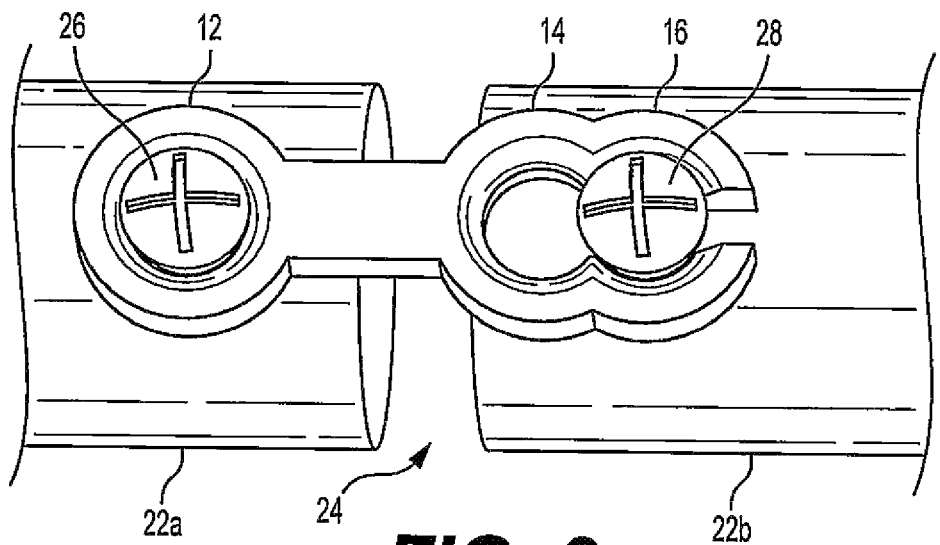
FIG. 2 is an environmental perspective view of the mini-plate of FIG. 1, shown attached across a bone fracture to fix the surgeon's alignment of the two pieces of bone.

As shown in FIG. 2, after alignment of the two pieces of the fractured bone, the surgeon uses a first screw 26 to attach the mini-plate to the left-hand piece 22a (in the orientation of FIG. 2) of the fractured bone, fixing the first screw 26 through the first ring 12. The surgeon then fixes the mini-plate to the right-hand piece 22b of the fractured bone on the opposite side of the gap 24 defined by the fracture line, using a second screw 28 inserted through the third ring 16 to finish fixing the mini-plate 10 to the the fractured bone.

Figure 3:
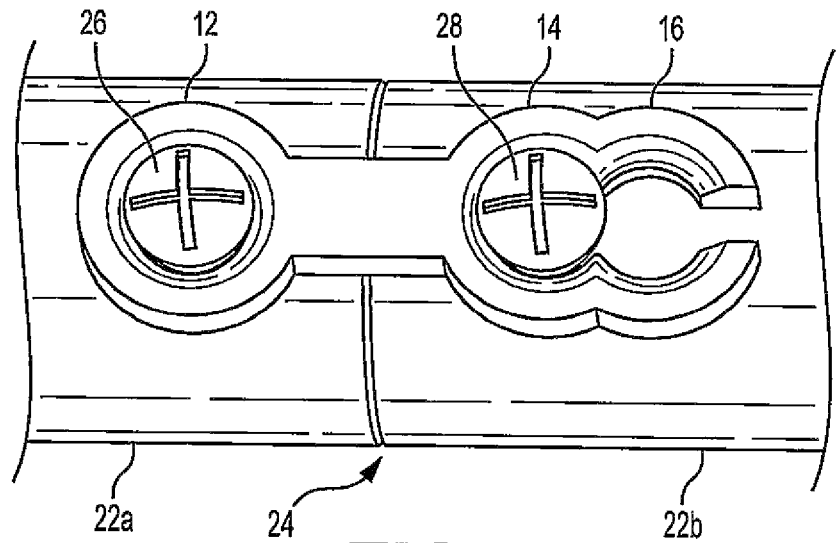
FIG. 3 is an environmental perspective view of the mini-plate of FIG. 2, shown after sufficient healing has occurred to permit the fixation screw installed in the third ring to slide forward into the second ring.

The fractured bone heals gradually over a period of time, knitting together to gradually close the gap 24 defined by the fracture line. As shown in FIG. 3, when the gap 24 has closed sufficiently, the shank of the second screw 28 below the head of the screw 28 may slide through the aligned gaps 18 defined in the second ring 14 and the third ring 16 (the aligned gaps 18 being dimensioned and configured to allow the shank of the screw 28 to pass through the gaps 18 while keeping the head of the screw 28 above the mini-plate 10), thus preventing holes or pores from developing in the union between the left-hand piece 22a and the right-hand piece 22b of the fractured bone as the bone heals. The outside gap 20 in the third ring 16 reduces drag to allow the sliding transition to occur smoothly, while also allowing expansion and adjustment, if needed.

It is to be understood that the mini-plate for bone fracture fixation is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A plate for bone fracture fixation, comprising a monolithic plate having a first ring fully enclosed therein, a second ring, and a third rings defined therein, the rings being configured linearly and dimensioned and configured to allow passage of shanks of internal fixation screws to pass through the rings while keeping heads of the internal fixation screws bearing against the plate, the plate being adapted for fixation to a fractured bone by a first internal fixation screw extending through the first ring into the fractured bone and a second internal fixation screw extending through the third ring into the fractured bone on opposite sides of the fracture, the second and third rings having aligned gaps defined therein dimensioned and configured to allow the shank of the second internal fixation screw to slide between the third ring and the second ring as the fractured bone heals and knits together.

2. The plate for bone fracture fixation according to claim 1, wherein said monolithic plate is made from a biocompatible material.

3. The plate for bone fracture fixation according to claim 1, wherein said third ring has an additional gap defined therein at a free end of the monolithic plate.

4. The plate for bone fracture fixation according to claim 1, wherein said monolithic plate has a length between four and five centimeters.

5. A method for internal fixation of a fractured bone, comprising:
   providing a plate according to claim 1; and
   inserting a first screw through the first fully enclosed ring of the plate into a first side of the fractured bone, such that a head of the first screw bears against the plate;
   inserting a second screw through the third ring of the plate into a second side of the fractured bone, such that a head of the second screw bears against the plate, and wherein the first and second sides of the fractured bone are separated by a gap defining a fracture in the bone.

* * * * *